United States Patent [19]

Bromberg

[11] 4,203,670
[45] May 20, 1980

[54] SYSTEM AND METHOD OF FLUORESCENCE POLARIMETRY

[76] Inventor: Nathan S. Bromberg, 461 Conant Rd., Weston, Mass. 02193

[21] Appl. No.: 789,636

[22] Filed: Apr. 21, 1977

[51] Int. Cl.² ............................................. G01N 21/40
[52] U.S. Cl. ..................................... 356/367; 356/365
[58] Field of Search .............. 356/103, 104, 114, 116, 356/117, 364, 366, 367, 369, 338, 339; 324/111, 140 D

[56] References Cited

U.S. PATENT DOCUMENTS

| | | | |
|---|---|---|---|
| 3,502,983 | 3/1970 | Ingle et al. | 324/140 D |
| 3,610,757 | 10/1971 | Van Valkenburg | 356/103 |
| 3,710,933 | 1/1973 | Fulwyler et al. | 356/104 |
| 3,850,525 | 11/1974 | Kaye | 356/103 |

OTHER PUBLICATIONS

Kay et al. "Twelve Functions in a New Digital Meter". *Hewlett-Packard Journal*, Mar. 1969, pp. 2-13.
Spencer et al. "Design, Construction, and Two Applications for an Automated Flow-Cell Polarization Fluorometer with Digital Read Out", *Clinical Chemistry*, vol. 19, No. 8, 1973, pp. 838-844.
Kelly et al. "Digital, Proton-Counting Fluorescence Polarometer", *Analytical Chemistry*, vol. 48, No. 6, May 1976, pp. 846-856.

*Primary Examiner*—John K. Corbin
*Assistant Examiner*—R. A. Rosenberger
*Attorney, Agent, or Firm*—Weingarten, Maxham & Schurgin

[57] ABSTRACT

A system and method for measurement of the polarization of fluorescence. A laser source provides a collimated linearly polarized beam of high intensity and small cross-section. A relatively small number of optical components are employed to minimize spurious fluorescence and spurious polarization which usually occurs from most optical materials. A photodetector provides an electrical signal in response to and representative of fluorescence polarization and is processed to directly produce first and second signals representing the difference and sum components of the polarization equation, the ratio of these components being directly provided without need for division computation.

39 Claims, 19 Drawing Figures

SYSTEM AND METHOD OF FLUORESCENCE POLARIMETRY

FIELD OF THE INVENTION

This invention relates to fluorescence polarization and more particularly to a system and method for measuring the magnitude of the polarization of fluorescence of solutions.

BACKGROUND OF THE INVENTION

The polarization of light emitted by an appropriately excited fluorescent solution can be defined by the intensity of two linearly polarized components, one vibrating along an axis orthogonal to the plane defined by the axes of the excitation light and the emitted light, and the other vibrating along an axis in that plane and orthogonal to the first component. If the first and second component intensities are respectively designated $I_\perp$ and $I_\parallel$, the polarization of the fluorescent emission is $$P = \frac{I_\perp - I_\parallel}{I_\perp + I_\parallel}$$

The measurement of the polarization of fluorescence is useful in the study of immune reactions and in biological assay and is also more generally useful for molecular analysis. For example, the polarization of fluorescence is of interest in the detection of change in molecular shape such as in protein denaturation, polymerization studies, monitoring of oil cracking reactions, and food process monitoring.

The following articles describe the measurement and some applications of polarization of fluorescence and apparatus for such measurement: G. Weber, "Photoelectric Method for the Measurement of the Polarization of the Fluorescence of Solutions," Journal of the Optical Society of America, Vol. 46, No. II, November 1956, pages 962–970; D. A. Deranleau, "A Recording Fluorescence Polarization Photometer," Analytical Biochemistry, Vol. 16, 1966, pages 438–449; R. J. Kelly, W. B. Dandliker and D. E. Williamson, "Digital, Photon-Counting Fluorescence Polarometer," Analytical Chemistry, Vol. 48, No. 6, May 1976, pages 846–856; R. D. Spencer, F. B. Toledo, B. T. Williams and N. L. Yoss, "Design, Construction, and Two Applications for an Automated Flow-Cell Polarization Fluorometer with Digital Read Out: Enzyme-Inhibitor (Antitrypsin) Assay and Antigen-Antibody (Insulin-Insulin Antiserum) Assay," Clinical Chemistry, Vol. 19, No. 8, 1973, pages 838–844; P. Johnson and E. G. Richards, "A Simple Instrument for Studying the Polarization of Fluorescence," Archives of Biochemistry and Biophysics, Vol. 97, 1962, pages 250–259; S. Ainsworth and E. Winter, "An Automatic Recording Polarization Spectrofluorimeter," Applied Optics, Vol. 3, No. 3, March 1964, pages 371–383; R. F. Chen and R. C. Bowman, "Fluorescence Polarization: Measurement with Ultraviolet - Polarizing Filters in a Spectrophotofluorometer," Science Vol. 147, 1965, pages 724–731.

In a known system for polarization of fluorescence measurement, a polarizer is aligned first along an axis parallel to the polarization axis of the excitation light and next along an axis orthogonal to the polarization axis of the excitation light, and orthogonal to the first axis, a measurement of the intensity of emitted fluorescent light being made for each polarizer position. A computation is then made of the sum and difference components and the ratio therebetween according to the above equation. A polarizer can be employed which is moved between two mutually orthogonal positions, as shown in the above-identified article of Chen and Bowman, or continuously rotated, as shown in the article of Kelly, Dandliker and Williamson. Alternatively, plural optical channels have been employed, as shown in Weber, each channel having polarized light respectively polarized in one of the two orthogonal positions. The vertically and horizontally polarized light is received by either a single photomultiplier tube or a separate photomultiplier tube for each channel. Often, an additional photomultiplier is employed to monitor the intensity of the excitation source for use in an automatic gain control circuit.

The system implementations known in the art have been quite complex both with respect to the optical arrangements employed and the electronic circuitry for computing polarization. Computation of the polarization equation has in general been accomplished by analog or digital computer or specific ratio determining apparatus such as a ratio recorder.

SUMMARY OF THE INVENTION

In brief, the present invention provides a system and method for measurement of the polarization of fluorescence capable of producing in a reliable, repeatable and accurate manner, measurements of even extremely small polarization of low level fluorescence. The invention employs a relatively small number of optical components to minimize the spurious fluorescence, spurious polarization and spurious scatter which can often occur from most optical materials, and employs a CW laser as a collimated and linearly polarized source providing a relatively high intensity input beam of small cross-section. On the excitation side of a sample, no lenses, separate polarizers or collimators need be employed, thereby eliminating optical components which, if present, could affect the polarization and background fluorescence. Only a single optical path is employed for both polarization components such that both components are equally affected by the common path, with the result that effects of the path can be cancelled by the signal processing.

The electrical signal provided in response to and representative of the polarization of fluorescence of light emitted from a sample is processed by relatively simple circuitry which provides an accurate output measurement. The signal processing circuitry directly produces first and second signals representing the difference and sum components of the polarization equation, and the ratio of these components is provided without actual division computation to thereby simplify the computational aspect of the signal processing.

DESCRIPTION OF THE DRAWINGS

The invention will be more fully understood from the following detailed description taken in conjunction with the accompanying drawings, in which.

DETAILED DESCRIPTION OF THE INVENTION

Figures 1, 3A, 10, 11, 12:
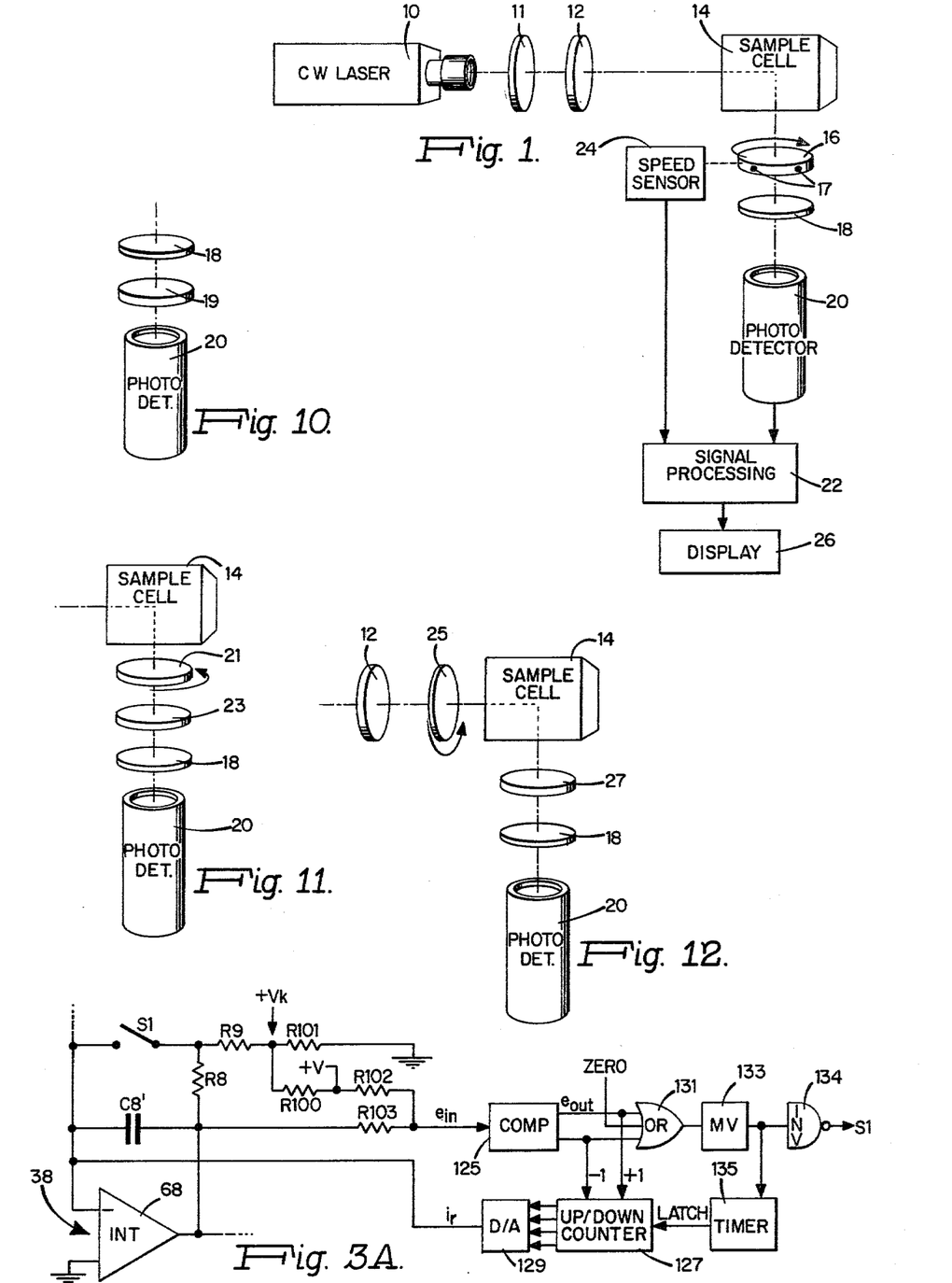
FIG. 1 is a diagrammatic view of a fluorescence polarimeter according to the invention.
FIG. 3A is a schematic diagram of the autozero logic of FIG. 3.
FIG. 10 is a diagrammatic view of an alternative embodiment of FIG. 1 employing a depolarizer.
FIG. 11 is a diagrammatic view of an alternative embodiment of FIG. 1 employing a half-wave plate or other rotating analyzer on the emission side of the sample cell.
FIG. 12 is a diagrammatic view of an alternative embodiment of FIG. 1 employing a rotating analyzer on the excitation side of the sample cell.

Referring to FIG. 1, there is shown a CW laser 10 providing a collimated source of linearly polarized monochromatic light through a filter 12 having an optical passband centered about the fundamental frequency of laser 10 and operative to exclude light above and below the frequency band of interest. A shutter 11 can be provided in front of laser 10 to occlude the beam except during a measurement run. Light from filter 12 is directed to a sample cell 14 which contains a liquid sample, the polarization of fluorescence of which is to be measured. Fluorescent radiation is emitted from the sample along an axis orthogonal to the axis of the light incident on the sample. Fluorescent radiation from sample cell 14 is directed through a continuously rotating linear polarizer 16 and thence through a filter 18 having a passband centered at the emission frequency.

Light transmitted by filter 18 is received by a photodetector 20, typically a photomultiplier tube, the electrical output signal of which is applied to signal processing circuitry 22. The rotational position and velocity of polarizer 16 is sensed by a sensor 24 which provides an electrical signal representative of the rotary position and velocity of polarizer 16 to circuitry 22 for use as a synchronizing signal, as will be explained. In typical embodiment, sensor 24 includes a magnetic or optical sensor operative to sense magnetic or optical elements 17 disposed about the periphery of polarizer 16 and to provide electrical pulses representative of the rotational position and speed of the polarizer 16. The output signal from circuitry 22 is applied to a display 26, such as a numerical indicator, for denoting the polarization of fluorescence of the sample under investigation. The output signal can also be applied to a printer, computer or other output device for storage or use.

The sample cell 14 is of known construction providing a temperature stabilized chamber for containing a quantity of sample liquid. By reason of the small cross-sectional area of the laser beam employed in the invention, the sample quantity can be quite small, about 3 microliters typically. The analysis time will vary depending on the nature of the sample, the intensity of the laser beam, and the accuracy required. This time can vary from fractions of a second to tens of seconds. The analysis is nondestructive such that repeated measurements can be made on a sample and no damage occurs to the sample.

Figures 2, 4A, 4B, 4C, 4D, 4E, 4F, 4G, 6:
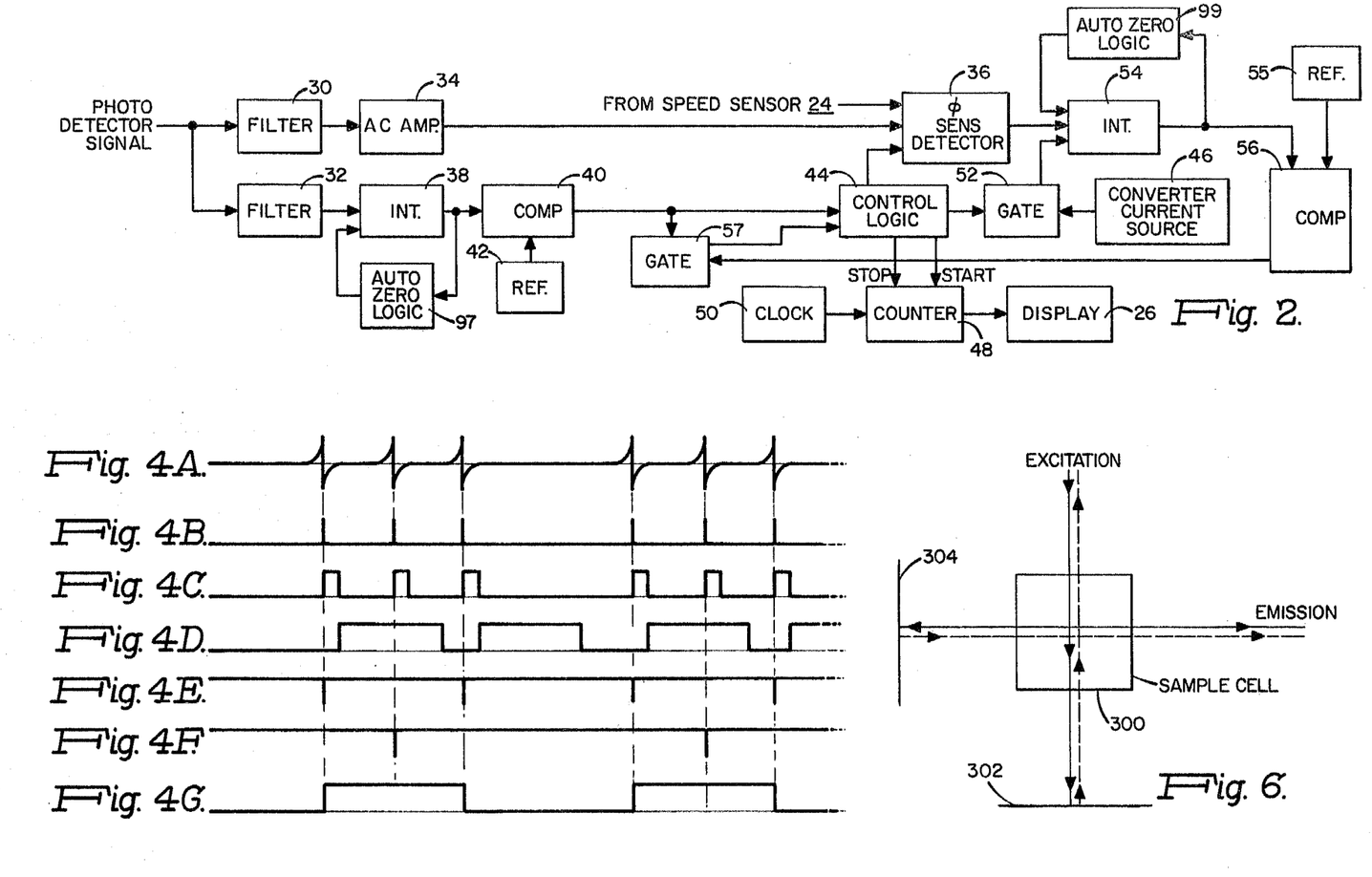
FIG. 2 is a block diagram of the signal processing circuitry of the invention.
FIGS. 4A-4G are waveforms useful in illustrating operation of the synchronizing pulse logic of FIG. 3.
FIG. 6 is a diagrammatic view of an alternative sample cell arrangement.

The signal processing circuitry 22 is shown in block diagram form in FIG. 2. The signal from the photodetector 20 is applied to filters 30 and 32. Filter 30 is a bandpass filter having a center frequency at twice the nominal rotational frequency of the rotating polarizer, and providing an output signal directly representative of the difference component of the fluorescence polarization and which signal is applied to an AC amplifier 34 and thence to a phase-sensitive detector 36. The filter 32 is a lowpass filter providing an output signal directly representative of the sum component of the fluorescence polarization and which signal is applied to an integrator 38 providing an integrated signal which is applied to one input of a comparator 40, the second input of which is a reference signal derived from an appropriate reference source 42. The output signal from comparator 40 is applied to logic 44 which provides an inhibit signal to phase-sensitive detector 36. Signals are provided by logic 44 to a counter 48 having an associated clock 50, the counter driving display 26. The filters 30 and 32 also serve to discriminate against 60 cycle and 120 cycle noise produced by the power line. Filter 30 prevents odd harmonics of the carrier frequency from being detectable by the phase-sensitive detector and prevent saturation of amplifier 34. The filter 30 bandwidth is sufficient to yield intended flat response within which speed regulation of the rotating polarizer can be achieved.

A frequency reference signal is provided by sensor 24 (FIG. 1) to phase-sensitive detector 36. The output of detector 36 is coupled to an integrator 54, the output of which is applied to a comparator 56 having an appropriate reference source 55. A converter current source 46 is coupled by gate 52 to integrator 54 in response to a control signal from logic 44. The output signal from comparator 56 is applied to gate 57, also receiving the output signal from comparator 40, the output of which is applied to logic 44.

Preferably, autozero circuits are provided in association with integrators 38 and 54 to compensate for variable offsets which may be present. The output of integrator 38 is applied to autozero logic 97, the output of which is applied as a compensating signal to integrator 38. Logic 97 is operative during an autozero cycle, as further explained below, to derive a compensating signal to substantially cancel the measured offset. Similarly, logic 99 provides autozeroing of integrator 54.

A DC and an AC component are respectively derived from the photodetector signal, the DC component representing the sum term of the polarization equation while the AC component represents the difference term. The DC component, after filtering by filter 32, is integrated in integrator 38. The AC component is converted by synchronous detection in detector 36 to a DC signal which is then integrated by integrator 54. When the output signal from integrator 38 reaches the level of the reference voltage from source 42, as determined by comparator 40, a start signal is provided by the comparator to counter 48 by way of logic 44 to cause counter 48 to accumulate the pulses from clock 50. This signal from comparator 40 also causes logic 44 to provide a gating signal to gate 52 to cause application of a constant current signal from source 46 to integrator 54 in place of the previously applied output signal from phase-sensitive detector 36. The constant current signal is of opposite polarity to the signal from detector 36 previously applied to integrator 54, such that the integrator 54 is caused to discharge at a uniform rate. Integrator discharge continues until a reference voltage, typically zero, is reached, as determined by comparator 56, which thereupon provides a stop signal via logic 44 to counter 48 to discontinue the counting operation. The count accumulated by counter 48 is representative of the discharge time of integrator 54 which in turn is representative of polarization. The accumulated count is applied to display 26 for numerical presentation of the polarization measurement.

It will be appreciated that integrator 54 in conjunction with counter 48 operates in the manner of a dual slope analog-to-digital converter in which the integrator is charged to a level representative of an input quantity to be measured and discharged at a uniform rate, the duration of discharge being representative of the input magnitude and during which discharge interval, a counter is caused to run to provide a digital indication of such magnitude. Here, integrator 54 is charged to a level determined by integrator 38, such that the discharge interval represents the ratio of the AC signal representing the difference term of the polarization equation, to the DC signal representing the sum term. Gate 57 is operative to inhibit comparator 56 operation to prevent spurious comparator switching in the presence of very low signal levels in the difference channel. Comparator 56 is disabled by having its output grounded by gate 57 when integrator 38 is charging and comparator 40 is untriggered.

The polarization is defined as the difference component divided by the sum component, and for each measurement the difference component measurement is made for a fixed number of sum component photons. The denominator of the equation is always the same and thus an actual division need not be performed, but the ratio is automatically provided which is proportional to the polarization. The counter 48 is started by the signal from comparator 40 while the counter is stopped by the signal from comparator 56. A count is provided for a normalized denominator value to provide a counter signal to display 26 which is a direct measure of polarization without requiring an actual computation of the division between the difference and sum terms of the equation.

Figure 3:
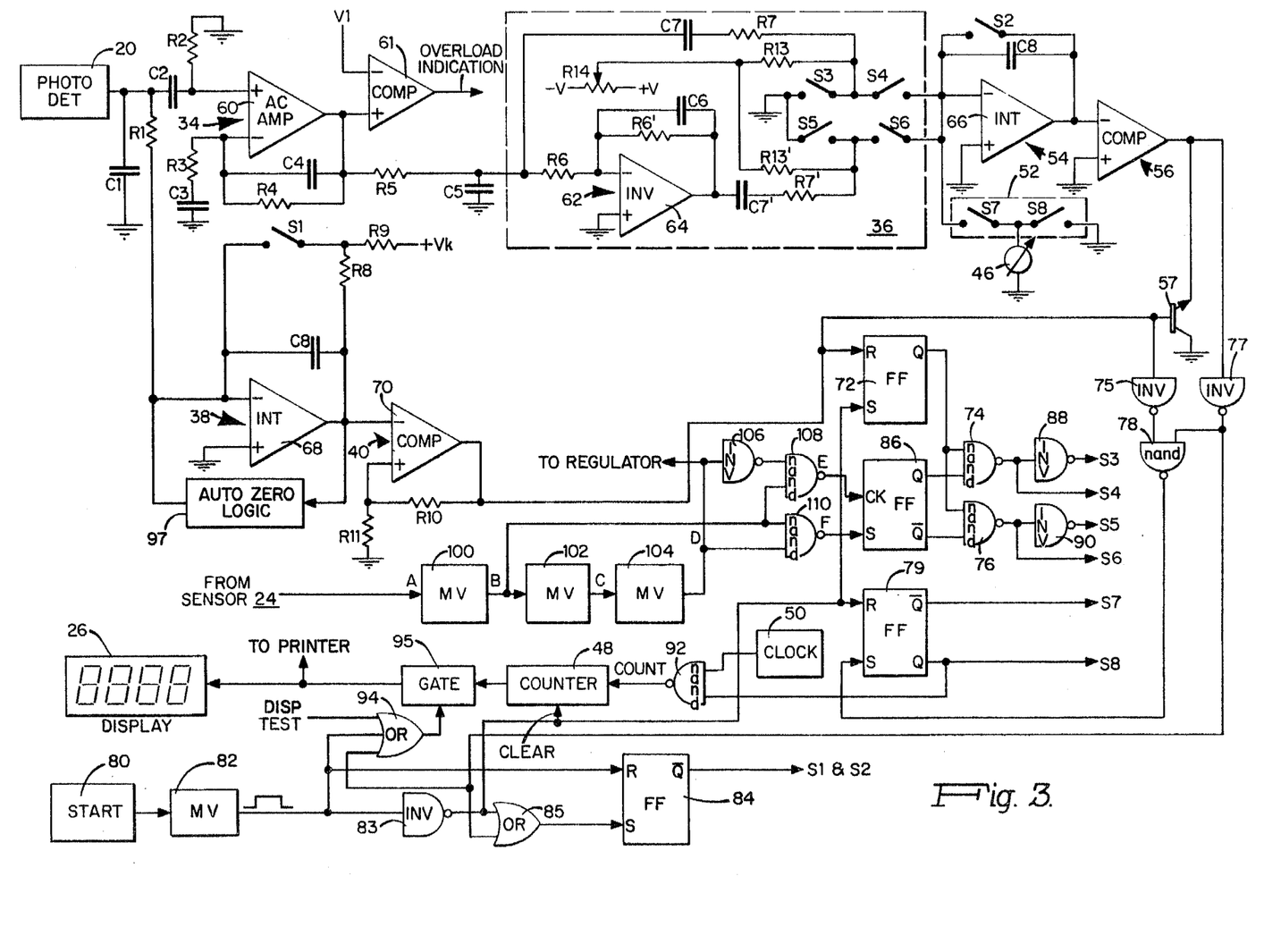
FIG. 3 is a schematic diagram of the signal processing circuitry of FIG. 2.

The signal processing circuitry is shown in greater detail in FIG. 3. The signal from the photodetector is applied to an input filter which includes capacitors C1, C2, C3, C4, C5, C7 and C7' and resistors R1, R2, R3, R4, R5, R7 and R7' connected as shown. The input filter includes filters 30 and 32 of FIG. 2, but not necessarily as distinct filter components. The capacitors C1 and C2 in association with resistors R1 and R2 serves as a lowpass filter, as does capacitor C4 and resistor R4, while further lowpass filtering is provided by capacitor C5 and resistor R5. Highpass filtering is provided by capacitor C2 and resistor R2, by capacitor C3 and resistor R3, and capacitors C7 and C7' and resistors R7 and R7'. The combination of capacitor C6 and resistor R6' provided in shunt with operational amplifier 64 is substantially for purposes of operational amplifier stability.

The AC component of the input signal is coupled by way of capacitor C2 to the positive input of operational amplifier 60 which includes a feedback resistor R4 and feedback capacitor C4 connected between the output of operational amplifier 60 and the inverting input thereof, and a resistor R3 and capacitor C3 series connected from the inverting input of operational amplifier 60 to ground. This AC amplifier stage 34 functions as a voltage follower with gain at the frequencies of interest and with unity gain at other frequencies above and below the band of interest. The amplifier 60 is coupled to one input of a comparator 61, the other input of which is coupled to a reference source V1. The comparator 61 produces an output indication of an overload condition caused by input signal sufficiently large to saturate amplifier 60. The overload signal typically is applied to a visual or other suitable indicator. The output of operational amplifier 60 is coupled via a series resistor R5 and shunt capacitor C5 to the phase-sensitive detector 36 which includes a first channel composed of a capacitor C7 and resistor R7 series connected to a pair of switches S3 and S4, and an inverting channel composed of an operational amplifier inverter 62, and capacitor C7' and resistor R7' in series connection between inverter 62 and a pair of switches S5 and S6. The inverter 62 includes an operational amplifier 64 having its positive input coupled to ground and its negative input coupled via resistor R6 to the input signal at the junction of resistor R5 and capacitor C5, and a feedback network composed of resistor R6' and capacitor C6. One terminal of switches S3 and S5 is coupled to ground, while the second terminal of switches S3 and S5 is coupled to respective terminals of switches S4 and S6. The second terminals of switches S4 and S6 are coupled in common to integrator 54 which is implemented by operational amplifier 66 and capacitor C8 in feedback connection therewith. A switch S2 is provided across capacitor C8 and is employed to discharge the capacitor before and after a signal processing cycle to remove residual charge before a measurement run. Switches S7 and S8 alternately connect a calibrated current source 46 to integrator 66 or to ground. The switches S7 and S8 function as gate 52 of FIG. 2. The common terminal of switches S3 and S4 is coupled by way of a resistor R13 to the movable contact of a potentiometer R14. Similarly, a resistor R13' connects the common terminal of switches S5 and S6 to the potentiometer movable contact. The potentiometer R14 is connected between respective voltage sources +V and −V and provides a manual control for zero correction to compensate for constant offsets of the electronic circuitry, such as offsets due to switching transients of switches S3–S6 and offset current and voltage of integrator 54. The resistor R13 and R13' are of the same value and potentiometer R14 is adjusted to provide a compensating current of a magnitude and sense to substantially nullify the particular offsets present. Automatic nulling of the offset error can alternatively be provided by use of known autozero techniques.

The phase-sensitive detector 36 operates to provide a direct current version of the AC input signal. The output terminal of the detector, which is coupled to the negative input of operational amplifier 66, is maintained at virtual ground by the feedback action of this operational amplifier. With switches S4 and S5 closed and switches S3 and S6 open, the input signal is applied via capacitor C7 and resistor R7 to the input of integrator 54, while the signal from inverter 62 is grounded. With switches S3 and S6 closed and switches S4 and S5 open, the inverted input signal is provided via capacitor C7' and resistor R7' to the input of integrator 54, while the noninverted input signal is grounded. The series capacitor and resistor of each path of detector 36 serves as a highpass filter to block the passage of direct current and therefore block any offset voltage and to attenuate frequencies below the cut-off frequency of the filter. The integrator 54 integrates the detector output voltage to achieve theoretically optimum low pass filtering.

The photodetector signal is also applied via resistor R1 to the DC channel which includes integrator 38 composed of operational amplifier 68 and feedback capacitor C8'. The output of operational amplifier 68 is coupled via series resistors R8 and R9 to a source of voltage $+V_k$. A switch S1 is connected between the junction of resistors R8 and R9 and the negative input of operational amplifier 68. Before and after a signal processing cycle, switch S1 is closed to produce a negative voltage on capacitor C8' to cause a comparator output level of high logic level. When switch S1 is open, allowing capacitor C8' to become positively charged in response to a received signal from the photodetector, the comparator 70 switches to low logic level when the output signal from integrator 38 is equal to the reference level at the positive input to comparator 70. The switches S1 and S2 of the respective integrators 38 and 54 are operative together in response to control signals from the control logic 44, as will be further described below. The output of operational amplifier 68 is applied to the negative input of comparator 70 which, with its feedback resistor R10 and resistor R11 coupled between the positive comparator terminal and ground serves as comparator 40 with hysteresis.

The output of operational amplifier 66 is applied to the negative input of comparator 56, the positive input of which is applied to ground as a zero reference. The output of comparator 56 is connected to the emitter of a transistor serving as gate 57, the base being connected to the output of comparator 40. The collector of the gate transistor, rather than its emitter, is grounded to achieve better switching characteristics. A relatively high level input applied by comparator 40 to the base will cause coupling of the comparator 56 output to ground. With a relatively low base drive, the transistor is nonconductive and comparator 56 is coupled to counter 48 by way of the operating logic to be described.

The control logic 44 receives output signals from comparators 40 and 56 and its operative to provide control signals for governance of the switches S1 through S8 to produce a polarization measurement numerically indicative on display 26. The switches S1 through S8 are, in practice, solid state switches operative in response to an electrical control signal to switch between conducting and nonconducting states. Such switches are per se well known in the art. In the illustrated embodiment, a low logic level causes switch closure, while a high logic level causes switch opening.

The control logic includes a flip-flop 72, the reset terminal of which is coupled to the output of comparator 40, the output terminal Q being coupled to an input of NAND gates 74 and 76. The set terminal of flip-flop 72 is coupled to start logic which includes a start control 80 such as a switch coupled to a multivibrator circuit 82 the output of which is coupled to an inverter 83, to the reset terminal of a flip-flop 84, and to one input of an OR gate 94. The output of inverter 83 is applied to one input of an OR gate 85, the output of which is coupled to the set terminal of flip-flop 84. The $\overline{Q}$ output of this flip-flop provides control signals to switches S1 and S2. The output of inverter 83 is also coupled to the clear input of counter 48, to the set terminal of flip-flop 72, and to the reset terminal of flip-flop 79. The output of comparator 56 is coupled to an inverter 77, the output of which is coupled to an input of OR gate 85 and to an input of OR gate 94. The output of inverter 77 is also coupled to an input of NAND gate 78, the output of which is coupled to the set terminal of flip-flop 79. The other input of NAND gate 78 is coupled to the output of an inverter 75, the input of which is coupled to the base of gate transistor 57 and to the output of comparator 40.

A flip-flop 86 provides outputs Q and $\overline{Q}$ to respective inputs of NAND gates 74 and 76. The outputs of these gates 74 and 76 are respectively coupled to input of inverters 88 and 90. The output signals from gate 74 and 76 are applied to the control terminals of respective switches S4 and S6, while the output signals from inverters 88 and 90 are applied to control terminals of respective switches S3 and S5. The outputs Q and $\overline{Q}$ of flip-flop 79 are applied to the respective control terminals of switches S8 and S7. The output signal from OR gate 94 is applied to gate 95 to permit transfer of a count in counter 48 to display 26. The clock 50 is coupled to the counter by means of a NAND gate 92, which also receives an input signal from the Q output of flip-flop 79 and is enabled thereby to apply clock pulses to the counter. The clock remains energized at all times that the system is on to maintain stability and minimize transient conditions.

The autozero logic 97 is shown more particularly in FIG. 3A, and operates as a digital servo, with a positive or negative increment provided during successive cycles until null is achieved. This circuit receives an input signal from the output of integrator 38 and provides an output signal to the negative input of the integrator to adjust for variable offsets, such as the dark current of the photodetector, and operational amplifier bias and offset. This autozero circuit includes a comparator 125 coupled to the output of integrator 38 by a resistor R103 and coupled to the voltage source $+V$ via resistor R102. The comparator 125 provides first and second outputs to an up-down counter 127, the output of which is applied to a digital-to-analog converter 129, the analog output of which is coupled to the negative input of integrator 38. The comparator outputs are also coupled via an OR gate 131 to a multivibrator 133, the output of which is applied to a timer 135. The output of timer 135 provides a latch signal to counter 127. The output signal from multivibrator 133 also serves as a control signal for switch S1 of integrator 38.

Initially, switch S1 is closed and shutter 11 is closed to shield the illumination source. For an autozero cycle, a ZERO command is provided by a suitable control, causing multivibrator 133 to provide a high logic level output, and causing a low logic level from inverter 134 which closes switch S1. At the end of the multivibrator timing interval, multivibrator 133 provides a low logic level output, causing switch S1 to open, and triggering timer 135. Comparator 125 provides a positive output level as a first output if the input singal $e_{in}$, which is the integrator output signal, is greater than a positive reference threshold, and a negative output level as a second output if the input signal is less than a negative reference threshold. The positive output from comparator 125 causes incrementing of counter 127, by one count, while the counter is decremented by one count in response to a negative output from comparator 125. The count stored by counter 127 is converted by digital-to-analog converter 129 to a current which is applied to the input of integrator 38. The counter is successively incremented or decremented until the signal $e_{in}$ is within the tolerance range of comparator 125, at which time neither comparator output is provided. The then count stored in counter 127 is converted to a corresponding current to maintain the integrator output voltage at a level to compensate for offsets. Timer 135 is retriggered upon each receipt of a signal from multivibrator 133. The autozero cycle continues until a compensating current is produced which causes an integrator output signal within the tolerance range of comparator 125. When a null condition has been reached, timer 135 runs for its predetermined interval, at the end of which a latch signal is applied to counter 127 to maintain the then count from which the compensating current is derived. The timer 135 defines the timing interval for which the integrator 38 must remain within tolerance.

Figure 5:
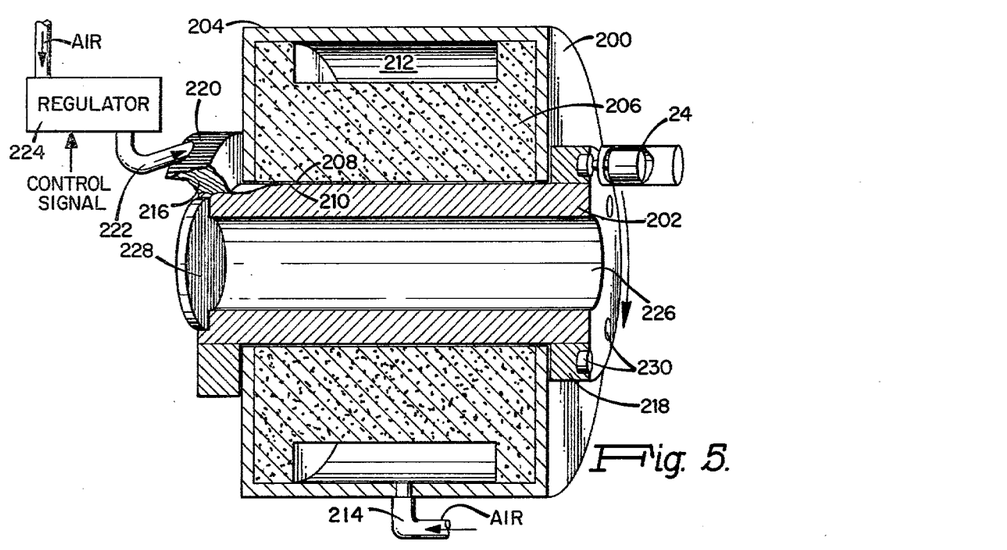
FIG. 5 is a partially cutaway pictorial view of a rotating polarizer employed in the invention.

Signals from the sensor 24 are applied to a pulse circuit 100 such as a Schmidt trigger, the output of which is applied to a multivibrator circuit 102, in turn coupled to a multivibrator circuit 104. The output of multivibrator 104 is coupled to an inverter 106, the output of which is applied to one input of NAND gate 108, the second input of which is received from the output of trigger circuit 100. The signal from circuit 100 is also applied to an input of NAND gate 110, the second input of which is the output signal from multivibrator 104. The output of gate 108 is applied to the clock terminal of flip-flop 86, while the output of gate 110 is coupled to the set terminal of flip-flop 86. The output signal from multivibrator 104 is also applied as a feedback signal to a regulator valve of the pneumatic speed control apparatus of the rotating polarizer, to be described. Typically, the trigger circuit 100 has a delay of one microsecond, while multivibrators 102 and 104 have delay times of 50 microseconds and 3 milliseconds respectively. This logic circuitry for providing synchronization pulses is associated with a rotating polarizer having six magnetic slugs disposed around the periphery of the polarizer, as shown in FIG. 5. Four slugs 17 are equispaced 90° apart around the perimeter, while two slugs are disposed across a diameter, each midway between an adjacent pair of slugs.

The synchronization logic operates as follows with reference to the waveforms of FIGS. 4A–4G. The waveforms are marked by associated letter designations in FIG. 3. The pulses provided by the sensor 24 are shown in FIG. 4A, and the signals provided in response to the sensor signals by Schmidt trigger circuit 100 are sharp pulses illustrated in FIG. 4B, each of the pulses being provided upon sensing passage of a magnetizable slug in the rotating polarizer. Each of the pulses provided by circuit 100 causes triggering of multivibrator 102 to provide pulses as depicted in FIG. 4C. The trailing edge of the pulses provided by multivibrator 102 cause triggering of multivibrator 104 which is of the non-retriggerable type such that once triggered the multivibrator operates for its predetermined time interval. Thus, the output pulses of multivibrator 104 are as shown in FIG. 4D. The output signal from multivibrator 104 serves to inhibit the provision of a clock pulse to flip-flop 86. Four sync signals are provided per revolution of the rotating polarizer, with two additional signals produced per revolution in order to provide intended phasing. Normally, the pulses (FIG. 4E) from gate 108 are regularly produced to clock flip-flop 86 which produces the Q signal (FIG. 4G) to drive the switches of phase-sensitive detector 36. If synchronization is lost or not yet established, as occurs during start-up of the system or as a result of spurious condition, only one-half revolution of the polarizer is needed to resynchronize. By the logic above described, in response to the pulses of FIG. 4B, the pulses of FIGS. 4E and 4F will become properly phased to appropriately clock flip-flop 86.

For operation of the system, it is preferable to leave laser 10, photodetector 20, rotating polarizer 16 and signal processing circuit 22 energized in order to minimize transients. The shutter 11 provided in front of laser 10 is closed to shield the light beam from sample cell 14, except during a measurement run in order to avoid heating or photodecomposition of the sample. To prolong laser life, full power can be applied to the laser only during an operating cycle, minimum power otherwise. Before a measurement run, an autozero cycle may be provided as described above. Next, the switches S1 and S2 are closed to initially condition the integrators 38 and 54 for the charging interval of a measurement cycle. During a measurement cycle, the switches S1 and S2 are open to permit charging of the associated capacitors. After display of a measurement, these switches are again closed to condition the associated capacitors for a subsequent measurement run. Before and after a measurement run, the switches S3 and S5 of phase-sensitive detector 36 are closed, while switches S4 and S6 are open. The input to integrator 54 is thereby open-circuited, while the output of detector 36 is shunted to ground to prevent any spurious signal from being applied to integrator 54.

Initially, the output of comparator 40 will be at a high logic level to cause gate 57 to couple the output of comparator 56 to ground irrespective of the inputs to comparator 56. The outputs of comparators 40 and 56 are coupled via inverters 75 and 77 and NAND gate 78 to flip-flop 79 which provides Q and $\overline{Q}$ outputs for respective control of switches S8 and S7. Switch S7 is open and switch S8 is initially closed before and after a measurement run and during an integration interval. Initially, flip-flop 72 provides an output signal of low logic level to gates 74 and 76, causing provision by these gates of high logic level outputs irrespective of the logic level of the signals from flip-flop 86. The signals provided by gates 74 and 76 to switches S4 and S6 are thus of high logic level to cause these switches to remain open, while the signals from inverters 88 and 90 are of low logic level to cause closure of switches S3 and S5.

Upon a start signal from source 80, multivibrator 82 goes high, causing a low output from inverter 83 which sets flip-flop 72 and resets flip-flop 79. Flip-flop 72 provides an output of high logic level to NAND gates 74 and 76 which produce respective output signals of logic level opposite to that of the respective signals from flip-flop 86. Thus, gates 74 and 76 and associated inverters 88 and 90 cause operation of switches S3 and S6 in unison, and switches S4 and S5 in unison, switches S4 and S5 being closed when switches S3 and S6 are open and vice-versa. After a delay interval provided by multivibrator 82 sufficient for discharge of capacitors C8 and C8' and sufficient to eliminate switching transients, flip-flop 84 is set to provide an output signal of high logic level to cause opening of switches S1 and S2. The start signal also clears counter 48.

The integrators 38 and 54 integrate the respective input signals thereto during an integration interval determined by detected fluorescent emission, integrator capacitance and reference voltage $V_k$. When integrator 38 goes high, comparator 40 goes low, resetting flip-flop 72, which causes, via gates 74, 76, 88 and 90, switches S4 and S6 to open and switches S3 and S5 to close. When comparator 40 goes low, gate 75 goes high, causing gate 78 to function as an inverter. Transistor 57 is nonconductive, allowing the output of comparator 56 to be applied to gate 77. If comparator 56 is low, gate 77 is high, and gate 78 goes low thereby setting flip-flop 79. Switch S7 is closed, and switch S8 is open. If comparator 56 goes high, gate 77 goes low, causing transfer of the then count in counter 48 to display 26 or other output device, by means of a transfer signal provided by gate 94 to gate 95. Flip-flop 84 is set, causing switches S1 and S2 to close.

When transistor 57 becomes nonconductive, comparator 56 could immediately go high if no signal has been accumulated by integrator 54, in which case counter 48 will have a zero count, since no time has elapsed in which to store a count, and this zero count will be transferred to the display to denote that a measurement of zero value has been made.

When integrator 38 reaches the comparator reference level, comparator 40 switches to provide an output signal of low logic level which causes flip-flop 79 to switch to provide closure of switch S7 and opening of switch S8 to commence a discharge interval. When the output signal from integrator 54 reaches the zero reference level, comparator 56 switches to provide an output signal of opposite (high) logic level to flip-flop 84 to cause closure of switches S1 and S2. The switching of comparator 56 also causes a transfer signal to be provided by gate 94 to gate 95 for transfer of the then count to display 26. This transfer signal can also be employed to energize a printer or other output apparatus for receipt of data from counter 48.

The counter 48 in the preferred embodiment remains running and is momentarily gated to display 26 or other output apparatus when an output reading is desired. The running counter can be utilized to visually test display 26 to verify the operability of the numerical indicators, which typically are multi-segment indicators, and operability of the display decoders.

For such testing, a display test signal provided by a suitable control is gated through gate 94 to cause coupling of the counter output to display 26, the transferred data from the counter causing energizing of the display indicators.

The rotating polarizer 16 is shown in a preferred embodiment of FIG. 5 and includes an air bearing having a stationary housing 200 and a rotor 202 disposed for rotation therein with minimum friction and vibration. True concentric rotation is important to reduce light beam modulation which can be caused by eccentric motion of the rotor, and to reduce mechanical vibration which can also cause modulation. In addition, the light beam is continuously passing through the same optical material during rotation, thereby minimizing modulation which could occur by variations in the material itself. The housing 200 is composed of a shell 204 having a core 206 of porous material, and having a cylindrical surface 208 confronting the cylindrical surface 210 of rotor 202. An annular chamber 212 is provided around the outer portion of core 206 and communicating with an air inlet 214 which is coupled to a source of air or other operating gas. Flanges 216 and 218 are provided around the respective ends of rotor 202 to retain the rotor 200 in the housing. A knurled surface 220 is provided about the periphery of flange 216, and an air nozzle 222 is disposed with respect to surface 220 to direct a jet of air or other operating gas onto the knurled surface to cause rotation of rotor 202. The air nozzle is coupled to a regulator 224 which in turn receives air from a suitable source. The regulator is operative in response to a control signal to adjust the flow of air to rotor 202 to maintain the speed thereof.

The control signal is derived from the synchronizing circuit of FIG. 3, which provides pulses derived from sensor 24, to achieve a closed loop speed control for the rotating polarizer. Regulation of the rotational speed of the polarizer is provided within an intended tolerance range. It is noted however, that regulation is not critical as a signal processing of the photomultiplier output signal is synchronous with the pulse rate of pulses derived from the rotating polarizer and variation can be tolerated within the bandwidth of the signal channels.

Air introduced into chamber 212 is diffused through porous core 206 to provide an air layer between surfaces 208 and 210 and provides an air bearing for the rotor. Air flowing out of the confronting space between the rotor and housing tends to maintain the rotor at a fixed axial position within housing 200. Such air bearings are per se known in the art and include confronting surfaces containing the air layer of very close tolerance. The rotor 202 includes an opening 226 axially therethrough, typically of about 1 centimeter diameter, with a polarizer plate 228 mounted at one end of the rotor. The polarizer element can alternatively be a prism mounted within the passage 226 of rotor 202. The light beam passes through the center of the polarizer, thus the same optical material is present during rotation. This is preferable to the use of a rotating polarizer in which the light beam passes through a peripheral portion of the polarizer which can be of varying optical characteristics.

Magnetic slugs 230 are mounted in openings provided in flange 218, six being illustrated, with four being equispaced about the circumference of the flange and two being diametrically disposed between respective pairs of slugs. The sensor 24, in this case a magnetic sensing device, is disposed adjacent flange 218 for providing an electrical signal in response to passage of each slug 230 by the sensor for provision of synchronizing pulses. The rotor 202 is of course nonmagnetic if magnetic slugs are employed as sensed elements. The sensor 24 is angularly adjustable about the circumference of rotor 202 to adjust the phase of the synchronizing pulses with respect to the photodetector signals being processed.

For the purpose of increasing the intensity of the exciting light incident on a sample, the alternative sample cell arrangement of FIG. 6 can be employed and which can also provide enhancement of the intensity of emitted polarized fluorescene received by the photodetector. Referring to FIG. 6, there is shown a sample cell 300 containing a sample to be measured, with a mirror 302 disposed to reflect the excitation beam and a second mirror 304 disposed to reflect the emitted fluorescene. The excitation beam is transmitted through the sample cell and after reflection by mirror 302 is retransmitted back through the sample cell to thereby increase the exciting energy absorbed by the sample, and provides a more uniform distribution of energy absorption throughout the sample volume. The exciting light is increased by approximately a factor of two. The emitted fluorescence transmitted toward mirror 304 is retransmitted toward the photodetector along with emitted fluorescene initially directed toward the photodetector, which further increases the detectable fluorescene. The mirror 304 can be constructed to be relfective at the emission wavelength and to be substantially nonreflective at other wavelengths which are not of interest for reception by the photodetector. The mirror 302 can also be constructed to be reflective only at the excitation wavelength, especially if a broadband source of illumination is employed, to reduce scatter. Such selectively reflective mirrors are per se known and can be fabricated by well known interference filter techniques. If no mirror 302 is employed, a light trap, known per se, is preferably employed to avoid excitation scatter.

Figure 7:
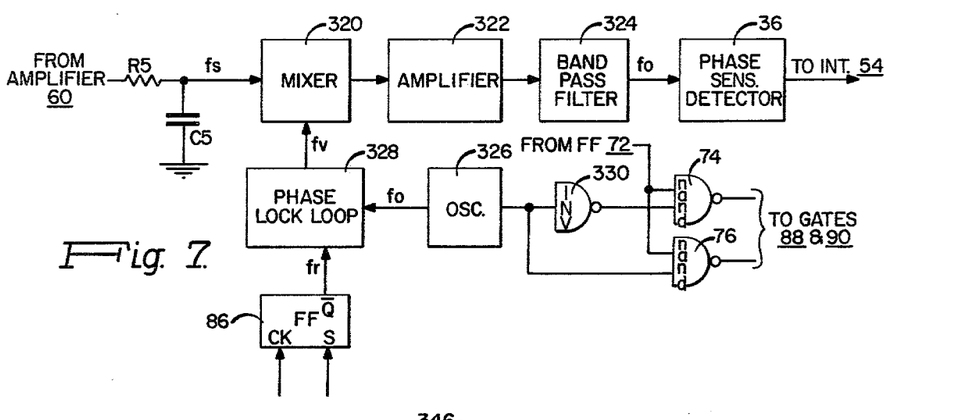
FIG. 7 is a block diagram of an alternative signal processing circuit.

As an alternative, the circuit of FIG. 7 can be employed to minimize the effects of variation in the rotational speed of the polarizer. As described above, the variation of speed of the rotary polarizer should be within the bandwidth limitations of the signal channel for precise signal processing. By the alternative embodiment to be presently described, further speed variation can be tolerated by use of a local reference signal derived from the synchronizing pulses from the rotary polarizer but independent of variation therein. With reference to FIG. 7, the signal from amplifier 60 (FIG. 3), is applied via lowpass filter composed of resistor R5 and capacitor C5 to a mixer 320, the output of which is applied to an amplifier 322 and a bandpass filter 324, the output of which is applied to phase-sensitive detector 36 of the circuitry of FIG. 3. An oscillator 326 provides a sinewave signal of frequency $f_o$ to a phase lock loop 328, the output signal of frequency $f_v$ being applied to mixer 320.

The phase lock loop also receives a reference signal $f_r$ from the $\overline{Q}$ output of flip-flop 86 (FIG. 3). The oscillator 326 also provides a squarewave signal of frequency $f_o$ to NAND gate 76 via an inverter 330 to NAND gate 74. The NAND gates 74 and 76 are the same as in FIG. 3 and provide signals to the switches S3–S6 of phase-sensitive detector 36 in the manner described above. The signal frequency $f_v$ provided by phase lock loop 328 is equal to the sum of the signals frequencies $f_o$ from oscillator 326 and $f_r$ from flip-flop 86. The output signal from mixer 320 contains sum and difference components of frequency $f_s$ and frequency $f_v$. The signal frequency $f_s$ equals frequency $f_r$ since both signals are derived from the rotating polarizer; the mixer output signal therefore contains signal component frequencies $f_o$ and $2f_r$. The bandpass filter 324 is of high Q centered at $f_o$ and thus provides a signal of frequency $f_o$ to the phase-sensitive detector 36. The amplifier 60 providing the input signal frequency $f_s$ in this embodiment can be of broader bandwidth than in the embodiment of FIG. 3. This circuit of FIG. 7 operates as a heterodyned lock-in amplifier which per se is known in the art. Means for phase calibration is provided as part of the lock-in amplifier. As employed in the invention, the phase-sensitive detector is supplied with a signal which is referenced to the oscillator 326 and signal processing is accomplished without affect by speed variation of the rotating polarizer.

The excitation filter 11 and emission filter 18 are constructed to avoid unwanted fluorescence, and to achieve this result these filters employ reflecting filter layers for both upper and lower bandwidth blocking rather than the more coventional absorbing glasses. The excitation filter 11 functions as a spike filter to pass only the excitation wavelength from laser 10, and to block by reflection all spurious wavelengths emitted by the laser, such as emitted by the gas plasma, and any ambient light leaks. The emission filter 18 functions to pass the emission band, and to block by reflection the scattered light at the excitation wavelength, as well as light at the Raman wavelength of the sample solution, and any other spurious wavelengths present.

Figure 8:
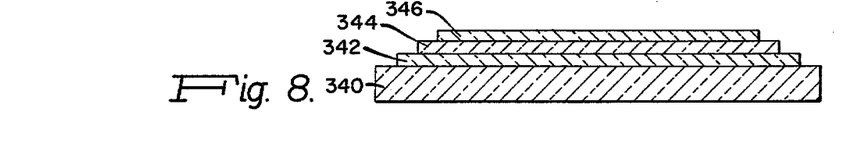
FIG. 8 is a greatly enlarged representation of an excitation filter employed in the invention.

The excitation filter is illustrated in FIG. 8 in a greatly enlarged scale and includes a substrate 340 of nonfluorescent quartz. A layer 342 is disposed on a surface of the substrate, this layer being an intereference filter which passes only the excitation wavelength, say 488 nanometers. A layer 344 reflects longer wavelengths, while layer 346 serves to reflect shorter wavelengths of the laser. Reflection is achieved by interference effects of the filter structure. It will be appreciated that the layers 342, 344 and 346 can actually be part of a sequential multiple coating optical filter structure or different interference combinations can be associated with respective substrates.

Figure 9:
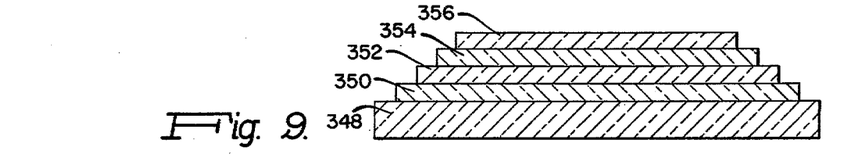
FIG. 9 is a greatly enlarged representation of an emission filter employed in the invention.

The emission filter is depicted in exaggerated scale in FIG. 9 and includes a substrate 348 of nonfluorescent quartz, having layers 350, 352, 354 and 356 thereon. The layer 350 provides a passband at the emission wavelength, and is an interference filter having its passband matched to the spectrum of the particular fluorescent dye employed. For fluorescene, the emission band is about 514 to 530 nanometers. The layer 352 serves to reflect the excitation wavelength, while layer 354 serves to reflect the Raman wavelength. Layer 356 provides a broadband reflection to block other unwanted wavelengths. Again, the filter layers described may actually be implemented as part of a multilayer filter structure.

A particular feature of the optical filters described above is the use of multiple reflecting layers for filtering, with no absorbing glasses being employed for filtering purposes. Such absorbing glasses can themselves fluoresce and thereby add spurious fluorescent emission within the band of interest. However, a glass layer may be employed as the last layer of the filter to serve as an attenuator, and in appropriate instances can provide absorption of unwanted wavelengths greater than the spurious emission in the band of interest. Referring to FIG. 10, an alternative embodiment of the invention is shown wherein a depolarizer 19, which preferably is a Lyot depolarizer or an opal glass diffuser, is disposed in front of the photodetector 20 to reduce any error caused by the polarization sensitivity of the photomultiplier tube. All photomultiplier tubes exhibit some plarization sensitivity, and the depolarizer 19 effectively scrambles the polarization of light transmitted therethrough such that nonpolarized light is received by the photodetector.

In the preferred embodiment described herein, a CW laser source is employed, however, other illumination sources can also be employed in practice of the invention. The source can be collimated or can otherwise be of minimum cross-sectional size and maximum band limiting, as is known. For example, an incandescent or other appropriate lamp can be provided in conjunction with a linear polarizer to produce a linearly polarized excitation beam which is then filtered by an excitation filter which is operative to exclude the particular spurious wavelengths present for the particular lamp. The illumination source can provide either polarized or nonpolarized light. In general, the use of linearly polarized excitation light is preferable for enhancement of the resultant polarization of fluorescence emitted by a sample. However, intended measurements can still be provided with unpolarized light as the exciting source.

It is contemplated that a continuously rotating analyzer, other than the linear polarizer described above, can be employed on either the excitation side of the sample cell or on the emission side thereof. Referring to the embodiment of FIG. 11, a nearly achromatic half-wave retardation plate 21 is disposed on the emission side of the sample cell 14 to receive fluorescent radiation therefrom, the plate being continuously rotatable such as by the pneumatic turbine described above, or other means. The half-wave retardation plate can be of any well known construction and is achromatic over the band of interest. A fixed linear polarizer 23 is disposed between plate 21 and filter 18 and is oriented with its polarization axis along an intended reference axis. A further alternative embodiment is shown in FIG. 12 in which a half-wave retardation plate 25 is disposed on the excitation side of the sample cell 14 and continuously rotatable. A fixed linear polarizer 27 is disposed between sample cell 14 and filter 18. The half-wave retardation plate 25 need function as such only at the laser wavelength since the laser source is monochromatic. The rotating analyzers such as shown in FIGS. 11 and 12 can also be electro-optical rotators, such as Faraday or Kerr rotators, providing optical rotation in known manner in response to an applied energizing signal, and constructed to function as a half-wave retardation plate or linear polarizer. The laser source or the photodetector could also themselves be rotated; however, this would not usually be practical because of the size and sensitivity of the source and the detector and because of the electrical connections thereto.

If an unpolarized excitation source is employed, a fixed linear polarizer must be provided if a half-wave retardation plate is to be used for rotation on the excitation side. In addition, when a half-wave retardation plate is employed, one cycle of mechanical rotation will provide four cycles of rotation of the polarization vector and the sensible elements provided about the periphery of the rotary structure, from which position and velocity signals are derived, should be arranged for each optical cycle, rather than employing two groups of three magnetic slugs or other sensible elements for each circumferential half of the rotary polarizer described above. A group of three sensible elements is located in each quadrant of the rotary half-wave retardation plate in order to provide phasing signals for each cycle of optical rotation.

The rotating analyzer can be continuously driven by means other than the pneumatic turbine described above. Rotation can alternatively be provided by an electric motor such as a synchronous motor of precise construction to achieve smooth rotation with minimum vibration. Such a synchronous motor drive can include a hollow rotor shaft to which the analyzer is mounted for rotation. If an electrically driven analyzer is employed, care must be exercised to minimize stray fields from affecting the photodetector. Placement of the electrical drive on the excitation side of the sample is usually preferred to increase the distance from the photodetector.

It will be appreciated that the signal processing circuitry also can be variously implemented. The invention does not require the use of dual slope integration techniques as described above, but can employ other circuit techniques for provision of an output measurement of polarization of fluorescence. For example, the integrator 54, which is charged to a level determined by the integrator 38, can be coupled to a sample and hold circuit triggered by comparator 40 to derive an output signal of a magnitude representative of polarization of fluorescence and which can then be processed to provide an output indication.

The present invention can also be employed for spectral analysis of emitted fluorescence. For such use a dispersing element such as a diffraction grating or prism is employed in place of the emission filter to produce a spectrum for analysis. If a laser is employed as the illumination source, means is provided for tuning of the source to a selected wavelength. Such tuning can be for selection of selected resonance wavelengths of the laser, or continuous tuning can be provided if a dye laser is employed. In addition to tuning of the laser source itself, a dispersing element can be employed at the excitation side of the sample. Excitation spectra can be provided by tuning on the excitation side; emission spectra can be provided by tuning on the emission side. If the excitation dispersing element is scanned, the observed emission wavelength is fixed. Alternatively, if the emission dispersing element is scanned, the exciting wavelength is fixed. Signal processing of the photodetector output signal can be accomplished as described above. In this embodiment, however, signal processing is accomplished for each pair of excitation and emission wavelengths to provide measurements to derive a spectrum.

In view of the many different optical configurations which can be employed in implementation of the invention, set forth below is a table outlining the various configurations:

| Source | Excitation Side of Sample | Emission Side of Sample |
| --- | --- | --- |
| Unpolarized | Filter | Rotating linear polarizer + depolarizer + filter or dispersing element |
| Unpolarized + depolarizer | Filter + rotating linear polarizer | Linear polarizer + filter or dispersing element |
| Polarized | Filter or dispersing element | Rotating linear polarizer + depolarizer + filter or dispersing element |
| Polarized | Filter or dispersing element | Rotating half-wave retardation plate + polarizer + filter or dispersing element |
| Polarized | Filter or dispersing element + rotating half-wave retardation plate | Polarizer + filter or dispersing element |

A depolarizer must be employed if a dispersing element is used and the viewed component is rotating, but is otherwise optional. The depolarizer on the excitation side or on the emission side is to achieve more ideal non-polarization if desired. The rotating linear polarizer can alternatively be an electro-optical rotator and a fixed linear polarizer. The rotating half-wave retardation plate can alternatively be an electro-optical rotator.

Use of a rotating element at the excitation side of a sample has several advantages. Since the excitation beam diameter is usually smaller than that of the emission beam, especially if a laser source is employed, the rotating element on the excitation side can be small. The collimation of the excitation beam also minimizes the criticality of the path length of the rotating element, which usually is the element of longest optical path.

Moreover, placement of the photodetector closer to the sample allows greater collection of light.

What is claimed is:

1. A fluorescene polarimeter comprising:
   an illumination source providing a defined, narrow band light beam;
   a sample cell for containing a sample solution and disposed to receive light from said illumination source and to permit fluorescent radiation from a sample solution;
   an analyzer;
   means for providing continuous rotation of said analyzer;
   an optical filter receiving fluorescent radiation from said sample cell and having a pass band centered at the emission frequency of said fluorescent radiation;
   photodetector means operative in response to radiation passed by said optical filter to provide an electrical output signal representative of radiation intensity;
   signal processor means operative in response to the output signal from said photodetector means and including;
   means for providing first and second signals respectively representative of the difference component and the sum component of fluorescence polarization;
   means providing a time interval representing the ratio of said first signal to said second signal and including:
   first integrator means receiving said second signal and providing a first integrated output signal;
   second integrator means receiving a signal derived from said first signal and providing a second integrated output signal of maximum level determined by the maximum level of said first integrated output signal; and
   means causing the discharge of said second integrator means at a uniform rate to provide said time interval; and
   means operative in response to said time interval to provide a signal representative of polarization of fluorescence.

2. The fluorescence polarimeter of claim 1 wherein said analyzer includes:
   an achromatic half-wave retardation plate disposed to receive fluorescent radiation from said sample; and
   a fixed linear polarizer receiving fluorescent radiation from said sample and having its polarization axis oriented along an intended reference axis.

3. The fluorescence polarimeter of claim 1 wherein said illumination source provides a linearly polarized light beam;
   and wherein said analyzer includes:
   a half-wave retardation plate disposed between said illumination source and said sample cell; and
   a fixed linear polarizer receiving fluorescent radiation from said sample and having its polarization axis oriented along an intended reference axis.

4. The fluorescence polarimeter of claim 1 wherein said analyzer includes a continuously rotated linear polarizer.

5. The fluorescence polarimeter of claim 1 further including a depolarizer disposed in front of said photodetector means to depolarize the light received thereby.

6. The fluorescence polarimeter of claim 1 wherein said analyzer includes:
   an electro-optical rotator disposed between said illumination source and said sample cell; and
   a fixed linear polarizer receiving fluorescent radiation from said sample and having its polarization axis oriented along an intended reference axis.

7. The fluorescence polarimeter of claim 1 wherein said analyzer includes:
   an electro-optical rotator disposed between said sample cell and said photodetector; and
   a fixed linear polarizer receiving fluorescent radiation from said sample and having its polarization axis oriented along an intended reference axis.

8. The fluorescence polarimeter of claim 1 further including at least one dispersing element disposed in the optical path between said source and said photodetector means and operative to provide a spectrum.

9. The fluorescence polarimeter of claim 1 wherein said time interval providing means includes:
   integrator means charged to a predetermined level and discharged at a uniform rate, the duration of discharge defining said time interval.

10. The fluorescence polarimeter of claim 1 wherein said illumination source includes a CW laser providing a collimated, monochromatic linearly polarized light beam.

11. The fluorescence polarimeter of claim 10 wherein said illumination source further includes a second optical filter receiving a light beam from said laser and having a pass band centered about the fundamental frequency of said laser and operative to exclude light above and below an intended band.

12. The fluorescence polarimeter of claim 11 wherein said second optical filter includes:
    an interference filter structure operative to pass only the excitation wavelength of said illumination source;
    an interference filter structure operative to reflect wavelengths longer than said excitation wavelength; and
    an interference filter structure operative to reflect wavelengths shorter than said excitation wavelength.

13. The fluorescence polarimeter of claim 1 wherein said signal processor means comprises:
    means for providing an AC signal directly representative of the difference component of fluorescence polarization;
    means for providing a DC signal directly representative of the sum component of fluorescence polarization;
    a counter;
    means operative in response to said DC signal to start operation of said counter;
    means operative in response to said AC signal to stop operation of said counter;
    said counter providing a count accumulated during the interval between said start and stop signals representing polarization of fluorescence.

14. The fluorescence polarimeter of claim 1 wherein said optical filter includes:
    an interference filter structure operative to provide a pass band matched to the spectrum of the fluorescent emission received;
    an interference filter structure operative to reflect the scattered light at the excitation wavelength;
    an interference filter structure operative to reflect light at the Raman wavelength of the sample solution; and an interference filter structure operative to reflect other spurious wavelengths of received light.

15. A fluorescence polarimeter comprising:
an illumination source providing a defined, narrow band light beam;
a sample cell for containing a sample solution and disposed to receive light from said illumination source and to permit fluorescent radiation from a sample solution;
an analyzer;
means for providing continuous rotation of said analyzer;
an optical filter receiving fluorescent radiation from said sample cell and having a pass band centered at the emission frequency of said fluorescent radiation;
photodetector means operative in response to radiation passed by said optical filter to provide an electrical output signal representative of radiation intensity;
signal processor means operative in response to the output signal from said photodetector means and including;
bandpass filter means providing a first signal directly representative of the difference component of fluorescence polarization;
lowpass filter means providing a second signal directly representative of the sum component of fluorescence polarization;
amplifier means coupled to said bandpass filter means and providing an amplified version of said first signal;
a phase sensitive detector receiving said amplified first signal and providing an output signal;
first integrator means operative in response to said second signal to provide a first integrated output signal
second integrator means operative in response to said output signal to provide a second integrated output signal;
first comparator means providing a first comparator output signal when said first integrated output signal exceeds a reference threshold;
second comparator means providing a second comparator output signal when said second integrated output signal exceeds a reference threshold;
means operative in response to said first comparator output signal to enable operation of said phase sensitive detector and operative in response to said second comparator output signal to disable operation of said phase sensitive detector;
counter means enabled in response to said first comparator output signal and disabled in response to said second comparator output signal;
means operative in response to said first comparator output signal to cause controlled discharge of said second integrator means to provide a time interval representing the ratio of said first signal to said second signal; and
means operative in response to said time interval to provide a signal representative of polarization of fluorescence.

16. The fluorescence polarimeter of claim 15 further including for each of said integrator means:
an autozero circuit operative to compensate for offsets.

17. The fluorescence polarimeter of claim 16 wherein said autozero circuit includes:
a comparator coupled to the output of said integrator means and providing a first output if the input signal thereto is greater than a positive reference threshold, and a second output if the input signal thereto is less than a negative reference threshold;
an up/down counter incremented by one count in response to said first output signal and decremented by one count in response to said second output signal;
a digital to analog converter operative in response to the output count from said counter to provide a compensating signal to the input of said integrator means; and
timer means triggered in response to an output from said comparator and operative to provide a latch signal to said counter at the end of its timing interval.

18. The fluorescence polarimeter of claim 15 wherein each of said integrator means includes:
switch means operative to shunt the integrator except during a measurement run to provide a predetermined stable condition.

19. The fluorescence polarimeter of claim 15 wherein said first integrator means includes:
an operational amplifier integrator circuit;
first switch means connected in shunt with said first integrator circuit and closed except during a measurement run;
and wherein said first comparator means includes:
an operational amplifier comparator circuit coupled to the output of said first integrator circuit and providing a first comparator output signal of first logic level when said first switch means is closed and of second logic level when said first switch means is open and the output signal from said integrator circuit equals the reference level of said first comparator means;
and wherein said second integrator means includes:
an operational amplifier integrator circuit;
second switch means in shunt with said second integrator circuit and closed except during a measurement run to remove residual charge on said second integrator circuit;
and wherein said second comparator means includes:
an operational amplifier comparator circuit coupled to the output of said second integrator circuit and providing a second comparator output signal of first logic level when said second switch means is closed and of second logic level when said second switch means is open and the signal from said second integrator equals the reference level of said second comparator.

20. The fluorescence polarimeter of claim 19 including:
gate means coupled to the output of said first and second comparator means and operative to disable said second comparator means when said first comparator output signal is of first logic level.

21. The fluorescence polarimeter of claim 15 wherein said controlled discharge means includes:
a current source;
means operative in response to said first comparator output signal to couple said current source to said second integrator means;
said current source providing a current of a polarity to cause discharge of said second integrator means.

22. The fluorescence polarimeter of claim 15 wherein said phase sensitive detector includes:

a calibration circuit operative to compensate for circuit offsets.

23. The fluorescence polarimeter of claim 15 including:
a comparator circuit coupled to the output of said amplifier means and providing an output indication of an overload condition in response to an input signal thereto greater than a predetermined threshold.

24. The fluorescence polarimeter of claim 15 further including:
a heterodyned lock-in amplifier having an oscillator providing a signal of predetermined frequency and providing a signal to said phase sensitive detector referenced to said oscillator signal and unaffected by speed variation of the rotating analyzer.

25. The fluorescence polarimeter of claim 15 further including:
a lowpass filter receiving a signal from said amplifier means;
a mixer receiving the output signal from said lowpass filter means and a reference signal;
a bandpass filter receiving the output signal from said mixer and providing an output signal to said phase sensitive detector; and
a phase lock loop providing said reference signal and receiving clock signals from an oscillator.

26. The fluorescence polarimeter of claim 15 wherein said phase sensitive detector includes:
first and second switch means closed before and after a measurement run to shunt the output of said detector to ground to prevent application of any spurious signal to said second integrator means;
third and fourth switch means opened before and after a measurement run to open circuit the input to said second integrator means;
during a measurement run said first and fourth switch means being operative to open and close in synchronism and said second and third means being operative to open and close in synchronism to provide phase sensitive detection.

27. The fluorescence polarimeter of claim 15 wherein said phase sensitive detector includes filter means operative to reduce power line and harmonic noise frequencies.

28. The fluorescence polarimeter of claim 1 wherein said phase sensitive detector includes:
switch means operative to shunt the detector output to ground except during a measurement run and to open circuit the input to said second integrator means except during a measurement run.

29. The fluorescence polarimeter comprising:
an excitation path having only
a laser source providing a collimated, monochromatic, linearly polarized light beam of small cross section and high intensity; and
a first optical filter receiving said light beam and having a pass band centered about the fundamental frequency of said laser source and operative to exclude light above and below an intended band;
a sample cell for containing a sample solution and disposed to receive light from said optical filter and to permit fluorescent radiation from a sample solution;
a linear polarizer disposed to receive fluorescent radiation emitted from a sample in said sample cell;
means for continuously rotating said linear polarizer;
a second optical filter receiving light from said rotating linear polarizer and having a pass band centered at the emission frequency of said fluorescent radiation;
photodetector means operative in response to radiation passed by said second optical filter to provide an electrical output signal representative of radiation intensity; and
signal processor means operative in response to said output signal to provide a signal representative of polarization of fluoresence;
and wherein said polarizer rotating means includes:
an air bearing having a housing and a hollow rotor disposed therein for rotation about an axis coincident with the axis of received fluorescent radiation;
said linear polarizer being mounted on said rotor symmetrical about said axis for rotation with said rotor;
pneumatic means providing an air layer between the confronting surfaces of said housing and said rotor; and
pneumatic means for directing a jet of air onto a surface of said rotor to cause rotation thereof.

30. The fluorescence polarimeter of claim 29 including:
sensor means disposed in operative association with said rotor;
a plurality of magnetic slugs disposed about a periphery of said rotor for sensing by said sensor means;
said sensor means providing control signals representative of the position and speed of rotation of said rotor.

31. The fluorescence polarimeter of claim 30 wherein said signal processor means includes means controlled by said control signals.

32. For use in a fluorescence polarimeter having an illumination source for exciting a sample solution, a continuously rotating analyzer, and a photodetector providing an output signal in response to fluorescent radiation received from the sample solution, a signal processor comprising:
means for providing first and second signals respectively representative of the difference component and the sum component of fluorescence polarization;
means providing a time interval representing a ratio of said first signal to said second signal and including:
first integrator means receiving said second signal and providing a first integrated output signal;
second integrator means receiving a signal derived from said first signal and providing a second integrated output signal of maximum level determined by the maximum level of said first integrated output signal; and
means causing the discharge of said second integrator means at a uniform rate to provide said time interval; and
means operative in response to said time interval to provide a signal representative of polarization of fluorescence.

33. The fluorescence polarimeter of claim 32 wherein said signal processor means comprises:
means providing an AC signal directly representative of the difference component of fluorescence polarization;

means for providing a DC signal directly representative of the sum component of fluorescence polarization;
a counter;
means operative in response to said DC signal to start operation of said counter;
means operative in response to said AC signal to stop operation of said counter;
said counter providing a count accumulated during the interval between said start and stop signals representing polarization of fluorescence.

34. A fluoresence polarimeter comprising:
an excitation path having only
a laser source providing a collimated, monochromatic, linearly polarized light beam of small cross section and high intensity; and
a first optical filter receiving said light beam and having a pass band centered about the fundamental frequency of said laser source and operative to exclude light above and below an intended band;
a sample cell for containing a sample solution and disposed to receive light from said optical filter and to permit fluorescent radiation from a sample solution;
an analyzer;
means for continuously rotating said analyzer;
a second optical filter receiving light from said rotating linear polarizer and having a pass band centered at the emission frequency of said fluorescent radiation;
photodetector means operative in response to radiation passed by said second optical filter to provide an electrical output signal representative of radiation intensity; and
signal processor means operative in response to said output signal to provide a signal representative of polarization of fluorescence;
and wherein said rotating means includes:
a hollow rotor disposed within a housing for rotation therein about an axis coincident with the axis of received fluorescent radiation;
said analyzer being mounted on said rotor symmetrical about said axis for rotation with said rotor;
means for providing rotation of said rotor about said axis;
a plurality of sensible elements disposed about the periphery of said rotor;
and control signal providing means including a transducer operative upon detection of said sensible elements to provide control pulses representative of the position and speed of said rotor.

35. The fluorescence polarimeter of claim 34 wherein said rotation providing means includes:
a regulator for governing the driving force applied to said rotor; and
means for providing a control signal to said regulator derived from said control pulses to provide servo control of rotor speed.

36. A fluorescence polarimeter comprising:
an illumination source providing a defined, narrow band light beam;
a sample cell for containing a sample solution and disposed to receive light from said illumination source and to permit fluorescent radiation from a sample solution;
an analyzer;
means for providing continuous rotation of said analyzer;
an optical filter receiving fluorescent radiation from said sample cell and having a pass band centered at the emission frequency of said fluorescent radiation;
photodetector means operative in response to radiation passed by said optical filter to provide an electrical output signal representative of radiation intensity;
signal processor means operative in response to the output signal from said photodetector means and including;
means for providing first and second signals respectively representative of the difference component and the sum component of fluorescence polarization;
means providing a time interval representing the ratio of said first signal to said second signal and including:
first integrator means providing a first integrated output signal in response to said second signal;
second integrator means providing a second integrated output signal in response to a signal derived from said first signal;
said second integrator means being operative for an integration time determined by the integration time of said first integrator means to cause a second integrated output signal of maximum level determined by the maximum level of said first integrated output signal; and
means causing the discharge of said second integrator means at a uniform rate to provide said time interval which represents the ratio of said difference component to said sum component and thus the polarization of fluorescence; and
means operative in response to said time interval to provide a signal representative of polarization of fluorescence.

37. For use in a fluorescence polarimeter having an illumination source for exciting a sample solution, a continuously rotating analyzer, and a photodetector providing an output signal in response to fluorescent radiation received from the sample solution, a signal processing method comprising the steps of:
deriving a first signal from said photodetector signal directly representing the difference component of fluorescence polarization;
deriving a second signal from said photodetector signal directly representing the sum component of fluorescence polarization;
integrating a signal derived from said first signal to a level determined by the level of a signal derived from said second signal;
causing controlled discharge of said integrated signal to provide a time interval representing the ratio of said first signal to said second signal; and
providing in response to said time interval a signal representative of polarization of fluorescence.

38. A fluorescence polarimeter comprising:
a laser source providing a collimated, monochromatic, linearly polarized light beam of small cross section and high intensity;
a first optical filter receiving said light beam and having a pass band centered about the fundamental frequency of said laser source and operative to exclude light above and below an intended band;
a sample cell for containing a sample solution and disposed to receive light from said optical filter and to permit fluorescent radiation from a sample solution;

an analyzer;

means for continuously rotating said analyzer;

a second optical filter receiving light from said rotating linear polarizer and having a pass band centered at the emission frequency of said fluorescent radiation;

photodetector means operative in response to radiation passed by said second optical filter to provide an electrical output signal representative of radiation intensity;

signal processor means operative in response to said output signal to provide a signal representative of polarization of fluorescence;

said signal processor means including:

means providing a first signal directly representative of the difference component of fluorescence polarization;

means for providing a second signal directly representative of the sum component of fluorescence polarization;

means operative in response to said second signal to denote the start of a time interval;

means operative in response to said first signal to denote the end of said time interval; and means operative in response to said time interval to provide an output indication of polarization of fluorescence.

39. The fluorescence polarimeter comprising:

a laser source providing a collimated, monochromatic, linearly polarized light beam of small cross section and high intensity;

a first optical filter receiving said light beam and having a pass band centered about the fundamental frequency of said laser source and operative to exclude light above and below an intended band;

a sample cell for containing a sample solution and disposed to receive light from said optical filter and to permit fluorescent radiation from a sample solution;

a linear polarizer disposed to receive fluorescent radiation emitted from a sample in said sample cell;

means for continuously rotation said linear polarizer;

a second optical filter receiving light from said rotating linear polarizer and having a pass band centered at the emission frequency of said fluorescent radiation;

photodetector means operative in response to radiation passed by said second optical filter to provide an electrical output signal representative of radiation intensity; and signal processor means operative in response to said output signal to provide a signal representative of polarization of fluorescence;

said signal processor means including:

bandpass filter means providing a first signal directly representative of the difference component of fluorescence polarization;

lowpass filter means providing a second signal directly representative of the sum component of fluorescence polarization;

amplifier means coupled to said bandpass filter means and providing an amplified version of said first signal;

a phase sensitive detector receiving said amplified first signal and providing an output signal;

first integrator means operative in response to said second signal to provide a first integrated output signal;

second integrator means operative in response to said output signal to provide a second integrated output signal;

first comparator means providing a first comparator output signal when said first integrated output signal exceeds a reference threshold;

means operative in response to said first comparator output signal to enable operation of said phase sensitive detector and operative in response to said second comparator output signal to disable operation of said phase sensitive detector;

counter means enabled in response to said first comparator output signal and disabled in response to said second comparator output signal;

means operative in response to said first comparator output signal to cause controlled discharge of said second integrator means;

wherein said polarizer rotating means includes:

an air bearing having a housing and a hollow rotor disposed therein for rotation about an axis coincident with the axis of received fluorescent radiation;

said linear polarizer being mounted on said rotor symmetrical about said axis for rotation with said rotor;

pneumatic means providing an air layer between the confronting surfaces of said housing and said rotor;

pneumatic means for directing a jet of air onto a surface of said rotor to cause rotation thereof;

sensor means disposed in operative association with said rotor;

a plurality of magnetic slugs disposed about a periphery of said rotor for sensing by said sensor means;

said sensor means providing control signals representative of the position and speed of rotation of said rotor; and said signal processor means including means controlled by said control signals.

* * * * *

UNITED STATES PATENT AND TRADEMARK OFFICE
CERTIFICATE OF CORRECTION

PATENT NO. : 4,203,670
DATED : May 20, 1980
INVENTOR(S) : Nathan Bromberg

It is certified that error appears in the above—identified patent and that said Letters Patent is hereby corrected as shown below:

Column 7,   line 26, "ground" should read --ground,--;

line 43, "its" should read --is--.

Column 12,  line 53, "fluorescene" should read --fluorescence--;

line 57, "fluorescene" should read --fluorescence--;

line 67, "fluorescene" should read --fluroescence--.

Column 13,  line 1,  "relfective" should read --reflective--;

line 63, "coventional" should read --conventional--.

Column 14,  line 47
                48, "plari-zation" should read --polari-zation--

Column 17,  line 4,  "fluorescene" should read --fluorescence--.

Column 25,  line 47, "rotation" should read --rotating--.

Signed and Sealed this

Eighth Day of December 1981

[SEAL]

Attest:

Attesting Officer

GERALD J. MOSSINGHOFF

Commissioner of Patents and Trademarks